United States Patent
Cowan et al.

(10) Patent No.: US 7,066,981 B2
(45) Date of Patent: Jun. 27, 2006

(54) ASSAYING METHOD

(75) Inventors: George M. Cowan, Boksburg (ZA);
Boyne F. Hohenstein, Boksburg (ZA);
Keith S. McIntosh, Boksburg (ZA);
Pierre K. Hofmeyer, Boksburg (ZA)

(73) Assignee: Innovative MET Products (PTY) Limited, Boksburg (ZA)

( * ) Notice: Subject to any disclaimer, the term of this patent is extended or adjusted under 35 U.S.C. 154(b) by 184 days.

(21) Appl. No.: 10/332,537

(22) PCT Filed: Jul. 12, 2001

(86) PCT No.: PCT/ZA01/00092

§ 371 (c)(1),
(2), (4) Date: Feb. 12, 2003

(87) PCT Pub. No.: WO02/04919

PCT Pub. Date: Jan. 17, 2002

(65) Prior Publication Data

US 2004/0025636 A1   Feb. 12, 2004

(30) Foreign Application Priority Data

| Jul. 12, 2000 | (ZA) | ................................ | 2000/2488 |
| Jul. 17, 2000 | (ZA) | ................................ | 2000/3576 |
| Mar. 16, 2001 | (ZA) | ................................ | 2001/2214 |
| Mar. 16, 2001 | (ZA) | ................................ | 2001/2216 |
| Jul. 17, 2002 | (ZA) | ................................ | 2000/3575 |

(51) Int. Cl.
*C22B 11/00* (2006.01)

(52) U.S. Cl. .......................... 75/631; 75/633; 75/637; 222/590; 266/227; 266/236

(58) Field of Classification Search .................. 75/377, 75/410, 637, 634, 375, 631, 633; 226/225, 226/270, 227, 236; 222/590; 228/51, 54, 228/60

See application file for complete search history.

(56) References Cited

U.S. PATENT DOCUMENTS

| 3,652,427 | A |   | 3/1972 | Flood et al. |
| 4,052,197 | A |   | 10/1977 | Brotzmann et al. |
| 4,274,622 | A | * | 6/1981 | Ohmori ....................... 266/227 |
| 4,373,705 | A | * | 2/1983 | Yamada ....................... 266/227 |
| 5,279,644 | A | * | 1/1994 | Francisco .................... 75/631 |
| 5,439,503 | A | * | 8/1995 | Burr ............................ 75/421 |

FOREIGN PATENT DOCUMENTS

WO   WO00/26664   5/2000

OTHER PUBLICATIONS

ASTM E-400-92a, Standard Test Method forSpectrographic Analysis of Ores, Minerals, and Rocks by the Fire Assay Preconcentartion Technique, American Society for Testing and Materials, published Sep. 1992.*

* cited by examiner

*Primary Examiner*—Roy King
*Assistant Examiner*—Kathleen A. McNelis
(74) *Attorney, Agent, or Firm*—Nixon & Vanderhye, P.C.

(57) ABSTRACT

The invention provides a method of assaying a mineral sample for determining the concentration of selected metals in a sample comprising the steps of providing a comminuted mineral sample; mixing such sample with a flux; preheating a reaction vessel to a temperature which approximates the melting point of the flux; introducing the mixture of the mineral sample and flux into the crucible, whereby the mixture is transformed to a molten state to capture the metal to be assayed in a collector material; and separating slag from the collector material.

24 Claims, 9 Drawing Sheets

ASSAYING METHOD

FIELD OF THE INVENTION

This application is the US national phase of international application PCT/ZA01/00092 filed 12 Jul. 2001 which designated the U.S.

THIS invention relates to assaying, and particularly, but not exclusively, to assaying gold and/or platinum group metals (PGM's), in an ore sample.

BACKGROUND TO THE INVENTION

It is common practice in gold or platinum mining and exploration operations to assay the ore in order to quantify the amount of gold and/or PGM's (platinum, palladium, rhodium, osmium, iridium and ruthenium) present.

The conventional assaying process is commonly known as "fire assay". The process involves weighing an amount of a comminuted ore, and mixing it with a lead oxide bearing flux or nickel flux. The mixture is then placed in a crucible and heated to elevated temperatures usually around 1100 to 1250 degrees Celsius for a period of about 60 to 90 minutes.

During this process the mixture melts, the lead oxide is reduced to lead metal or nickel sulfide is formed and the lead or nickel sulfide acts to collect the PGM's and/or gold due to their chemical affinity.

The molten slag and collector material is poured in to a mould where it is allowed to cool. The lead or nickel sulfide settles to the bottom of the mould. Once the mould is cooled, the lead or nickel sulfide is separated from the slag using mechanical techniques. The procedure is labour intensive. Once the collector material has been separated from the slag, it is placed in a cupel which is pre-heated at 1000 to 1300 degrees Celsius to allow the lead to be absorbed by the cupel. The result is a tiny prill left at the base of the cupel. The PGM's and gold content in the prill can then be determined using a number of analytical techniques.

Apart from the time consuming process described above, it has been found that during the loading and removal of reaction vessels or crucibles from a fire assay furnace considerable energy losses occur resulting in further delays in the assaying process.

Regarding the fluxes used in fire assay processes, conventional components of fluxes include borax (hydrated sodium borate), sodium carbonate, litharge (lead monoxide), silica, carbon, fluospar, red lead $Pb_3O_4$) potassium nitrate, and iron.

OBJECT OF THE INVENTION

The object of the present invention is to provide a new method of collecting metals in a mineral sample in an assaying process.

A further object of the present invention is to provide a methods and means for concentrating a metal collected in a collector and/or co-collector material.

A further object of the invention is the provision of methods and means for separating a metal collected in an assaying process, from a molten slag.

A further object of the invention is to provide a handling mechanism and method which is suitable for use in an assaying process.

Yet a further object of the invention is to provide a novel reaction flux for assaying which it is believed will have advantages over conventional fluxes.

A further object of the invention is to provide a handling mechanism and method suitable for loading and removing crucibles, reaction vessels or the like into and removing the same from a furnace.

SUMMARY OF THE INVENTION

According to the present invention, a method for assaying a mineral sample for determining the concentration of selected metals in the sample, comprises the steps of:

providing a comminuted mineral sample;

mixing such sample with a flux;

preheating a reaction vessel to a temperature which approximates the melting point of the flux;

introducing the mixture of the mineral sample and flux into the crucible, whereby the mixture is transformed to a molten state to capture the metal to be assayed in a collector material;

and separating slag from the collector material.

The collector material is preferably separated from the slag by allowing the collector material to drain through an outlet aperture by force of gravity, the dimensions of the aperture being sufficiently restricted to prevent the slag from draining through the aperture by force of gravity.

Further according to this aspect of the invention, heat energy is added to the reaction vessel and mixture once the latter has been introduced into the reaction vessel to cause fusion of the mixture.

In one embodiment of the invention, the collector material will be lead or other material capable of being oxidized, and a further method of the invention provides for the step of oxidizing such collector material to reduce the volume thereof, or a collector material. In such a method, the re-oxidized collector material will thus be recaptured by slag of the flux. This method may be applied to conventional assaying processes wherein the reaction vessel is not preheated.

In the above aspect of the invention, the collector material is oxidized by introducing oxygen, or an oxygen producing material, into the reaction vessel. Preferably, the oxygen will be introduced into the collector material by means of a lance or the like.

In an alternative arrangement the reaction vessel can be provided with a low level outlet and oxygen introduced into the reaction vessel through the low level outlet thereof for re-oxidizing collector material. Thereafter, the collector material can be drained through the low level outlet further analysis.

Also according to this aspect of the invention, the method may include the step of introducing a separate collector for the material to be assayed into the reaction vessel, such as silver or gold.

In an alternative arrangement the method of the invention may include the step of separating the collector material from the slag formed during the fusion process, and thereafter contacting the collector material with oxygen or oxygen forming material to oxidize the collector material or a portion thereof. In this arrangement it is preferable that a stream of oxygen gas will be blown onto, or into the collector material for oxidization purposes. Thus in the cases where collector material includes lead, such lead will be oxidized to lead oxide which will be released as a vapor. Collector material such as silver which is not capable of being oxidized readily, will remain for assaying purposes.

In a further example oxygen may be introduced into the separation vessel from a supply source via a collection mould which sealingly engages the separation vessel below the outlet duct therefrom.

Also according to this aspect of the invention, the method includes the step of disengaging the collection mould from the separation vessel to permit the collected material to drain into such collection mould. Pressure in the collection mould thus serves to close the outlet duct until the collection mould is disengaged from the separation vessel.

Once the collected material has been discharged into the collection mould, the material will be caused to fuse and to form a prill, and such prill can be deposited on a suitable transportation means for further processing.

Also included within the scope of the invention, is a apparatus suitable for use in the above method comprising a separation vessel, having a low level outlet duct, and a collection mould disposed below the outlet duct and adapted sealingly to engage the separation vessel, an inlet for oxygen or other gas in the collection mould to enable oxygen/gas to be ducted through the interior of the collection mould and the low level outlet duct, into the separation vessel.

Also according to this aspect of the invention, the apparatus includes lifter means whereby the collection mould can be lifted into engagement with the separation vessel, and lowered to a position removed from the separation vessel.

Preferably, the separation vessel will include a downwardly directed tube formation extending from the outlet duct, and against which the collection mould sealingly engages.

The invention further provides a method of separating the collector material from the slag, comprising the steps of providing a collector material which is of greater density and/or lower viscosity than the slag, providing a separating vessel which is provided with a outlet duct, and draining the collector material through such outlet duct, the arrangement being one wherein the dimensions of the outlet duct are such that the collector material passes therethrough, while the slag is arrested at the duct. Preferably the outlet duct will be disposed at the lower extremity of the vessel.

The invention is also directed separately to the separating vessel described above and in one embodiment thereof, the vessel is of a generally conical shape in cross-section, with the outlet duct being disposed at the lowermost pinnacle of the cone shape.

Where the collector material is lead, the outlet duct could for example be of a circular cross-section having a diameter of between 0.5 mm and 2.0 mm, preferably around 1.0 mm.

In an alternative arrangement, such a method of separating collector material from slag comprises the steps of providing a separating vessel which defines an interior concavity which terminates in a lower portion for receiving the collector material, and which defines an outlet duct in a position spaced from such lower portion, and comprising the further steps of rotating the reaction and separating vessel transversely so that collector material in the lower-most portion, flows to the zone of the outlet duct; and draining such collector material through the outlet duct. As previously mentioned the proportions of the outlet duct will be such that the collector material is capable of passing therethrough, while the slag is arrested.

With the above alternative method the vessel thus has a lower portion for receiving collector material and an outlet duct spaced from such lower portion, the outlet duct being such that the collector material is capable of passing therethrough, while the slag is arrested, and a concavity in the zone of the outlet duct for receiving the collector material when the reaction and separating vessel is rotated angularly to cause the collector material to flow to the zone of the outlet duct.

According to a different aspect of the invention a handling mechanism for transporting an article such as a reaction vessel or crucible into a furnace is provided comprising carrier means, the carrier means being movable between a first position in which it is displaced from the furnace and a second position in which it mates with an aperture in the furnace; and drive means for moving the carrier means between the first and second positions.

The handling mechanism described above is particularly suitable for use in the fire assaying methods of the invention. Accordingly, the article may comprise at least a crucible containing a mineral sample and a flux therein.

Preferably, the aperture is located in a base portion of the furnace and the carrier means is suitable for mating with the aperture when in the second position, effectively to close the aperture. Further, the handling mechanism according to the invention may include a loading device for transporting an article to the carrier means when the carrier means is in the second position. The loading device is preferably a robotic arm. The drive means is preferably a pneumatic reciprocating ram. Alternatively, the drive means may be a lever or a cam mechanism.

The invention further provides a furnace for use with the handling mechanism described above, the furnace having at least one aperture suitable for mating with the carrier means.

Separately included within the scope of the invention, is a process for heat treating an article for example in an assaying process comprising the steps of:
providing a furnace as described above;
moving the carrier means to the first position;
loading the carrier with an aticle;
moving the carrier means to the second position such that the article is carried into the furnace; and
removing the article from the furnace after the required residence time, by moving the carrier means to the first position.

According to yet a further aspect of the invention, a flux suitable for use in the fire assay methods of the invention includes a collector material adapted to combine with material in a mineral sample which is to be collected, and potassium hydroxide. For most applications, the flux will include between 5% and 60%, preferably 7.5% potassium hydroxide by weight.

Further according to this aspect of the invention, the flux includes one or more additional compounds selected from the alkaline earth metal group of compounds. Preferably, such alkaline earth metal group compounds will be hydroxides. Thus in one arrangement the flux may include between 5% and 60%, preferably 7.5% by weight of calcium hydroxide.

Also according to the invention, the flux may include one or more additional compounds from the alkaline metal group, preferably hydroxides. For example, the flux may include between 10% and 19% sodium hydroxide, by weight.

In order more clearly to illustrate the invention, some embodiments thereof are described hereunder, purely by way of example, with reference to the accompanying drawings wherein:

DESCRIPTION OF DRAWINGS AND EXAMPLES OF THE INVENTION

Figure 1:
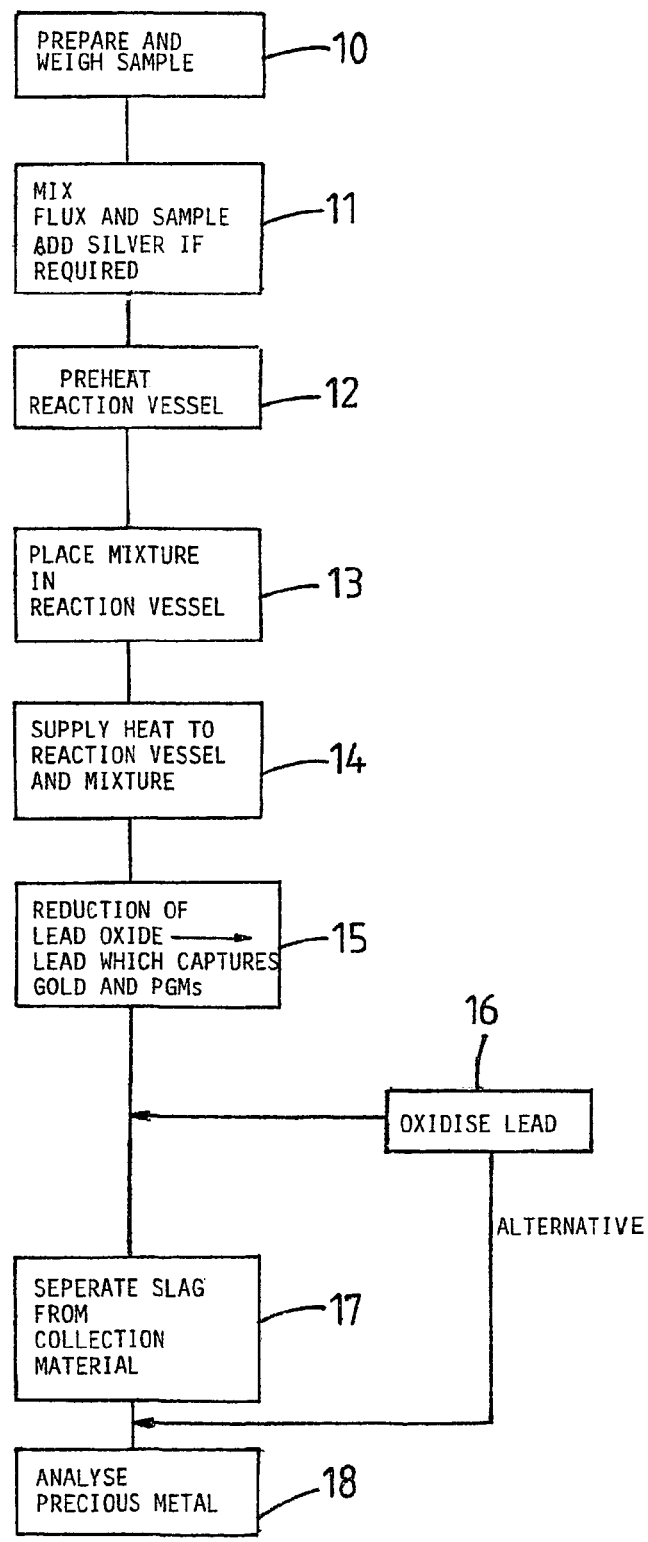
FIG. 1 is a flow diagram of a method of assaying in accordance with the invention.

Referring to the drawings, a method of assaying in accordance with the invention comprises the steps set out in FIG. 1. These steps comprise providing a mineral sample shown at 10, normally in dry powdered form, and mixing (11) a predetermined weight of such sample with a predetermined quantity of a suitable known flux which contains lead oxide, nickel or another material which is adapted to form a collector material for the analyte/metal mineral which is to be assayed. The method of the invention is in particular but not exclusively adapted for assaying gold or PGM's.

The mixture prepared as above, is next introduced into a reaction vessel (13). It is a feature of the invention that the reaction vessel will be pre-heated (12) to a temperature in the region of the fusion temperature of the mixture, in a suitable furnace or the like. Such furnace could for example be gas fired, electric or an induction furnace. Upon introduction of the mixture into the reaction vessel, further heat energy is supplied to the reaction vessel as shown at 14 to maintain it at the fusion level of the mixture.

Upon fusion of the mixture, a collector material, such as lead or nickel sulfide, is formed at 15 and acts to collect the gold and PGM's through chemical affinity. The collector material can thereafter be separated from the slag as described below, for analysis.

Figure 2:
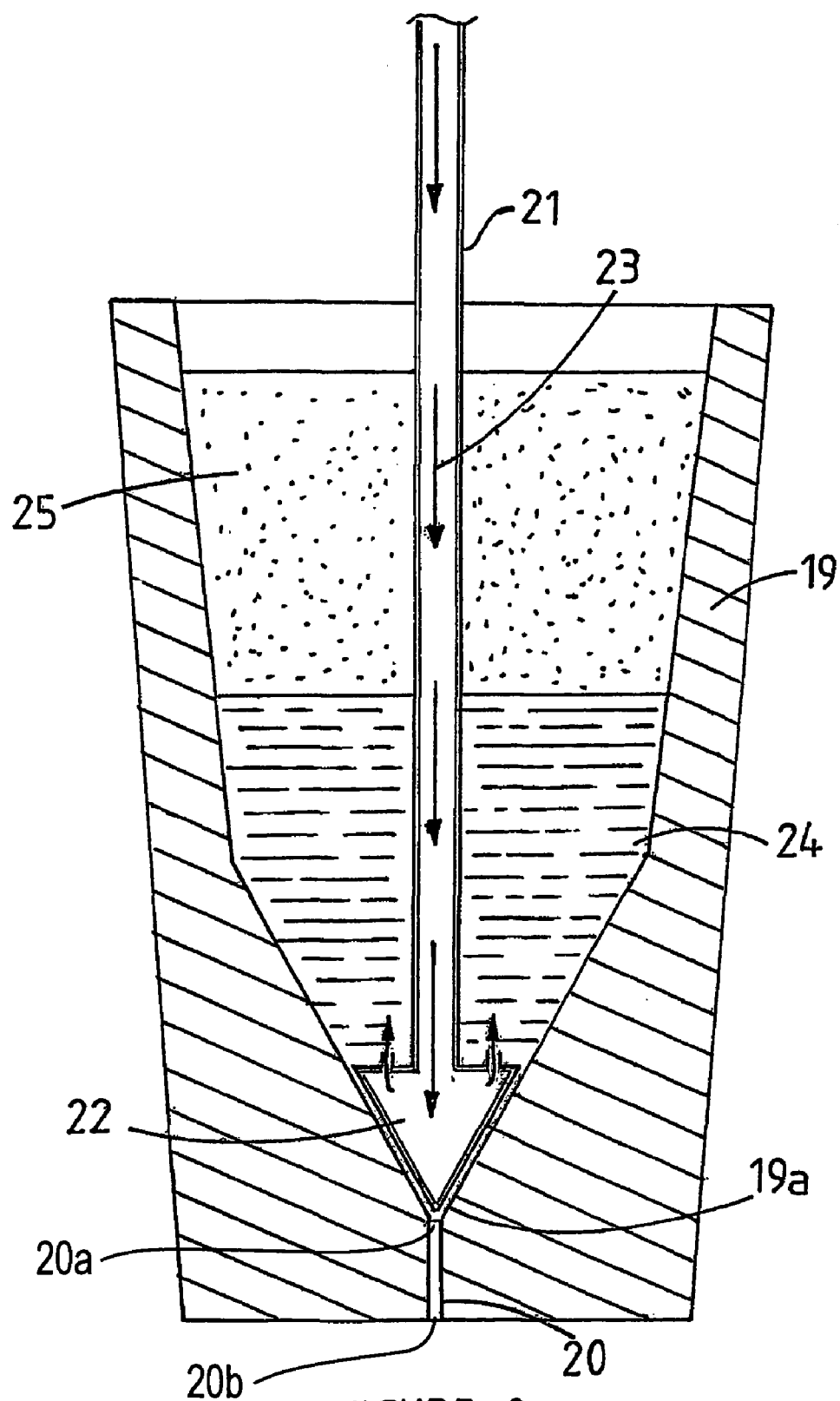
FIGS. 2 to 3 are schematic sectioned elevations of a reaction and separating vessel which is employed in the method of the invention, illustrating various steps in such method.

One aspect of the invention, provides for the collector material to be reduced in volume (16), and if necessary, to be concentrated by a co-collector material (17) in order to enhance the assaying process. Such reduction in volume is illustrated in FIG. 2 and comprises the step of introducing oxygen 23 into the collector material 24, FIG. 2, for example by means of a lance 21 which projects into the reaction vessel shown at 19, FIG. 2. The oxygen 23 thus reacts with the lead 24, or other collector material, which is capable of being oxidized, and oxidizes the lead to lead oxide which is recaptured in the slag 25. With this method, a small amount of lead 24 can be retained for assaying (18), or else, concentrated in a co-collector such as silver or gold which is more amenable to analysis, for example, by means of spark spectrometry. The invention thus envisages that a separate co-collector material could be added to the mixture prior to fusion or thereafter.

As an alternative to the use of the lance 21, the molten collector material 24 can first be separated from the molten slag 19 and deposited in a cupel in molten form, and at that stage contacted with a rich source of oxygen, whereby the collector material 24 is oxidized or partially oxidized. As previously mentioned, the collector material 24 can comprise lead which is readily oxidized in such conditions, together with silver as a co-collector which is not readily oxidized. During the oxidation process, the silver will thus remain to form a prill which contains the metal to be assayed. Such a prill will for example lend itself to analysis by gas release cromatographic analysis. Thus, this source of oxygen can again for example be in the nature of a lance 21 used for blowing oxygen gas onto or into the collector material 24, or alternatively, an oxygen producing salt can be introduced into the collector material 24.

Figure 9:
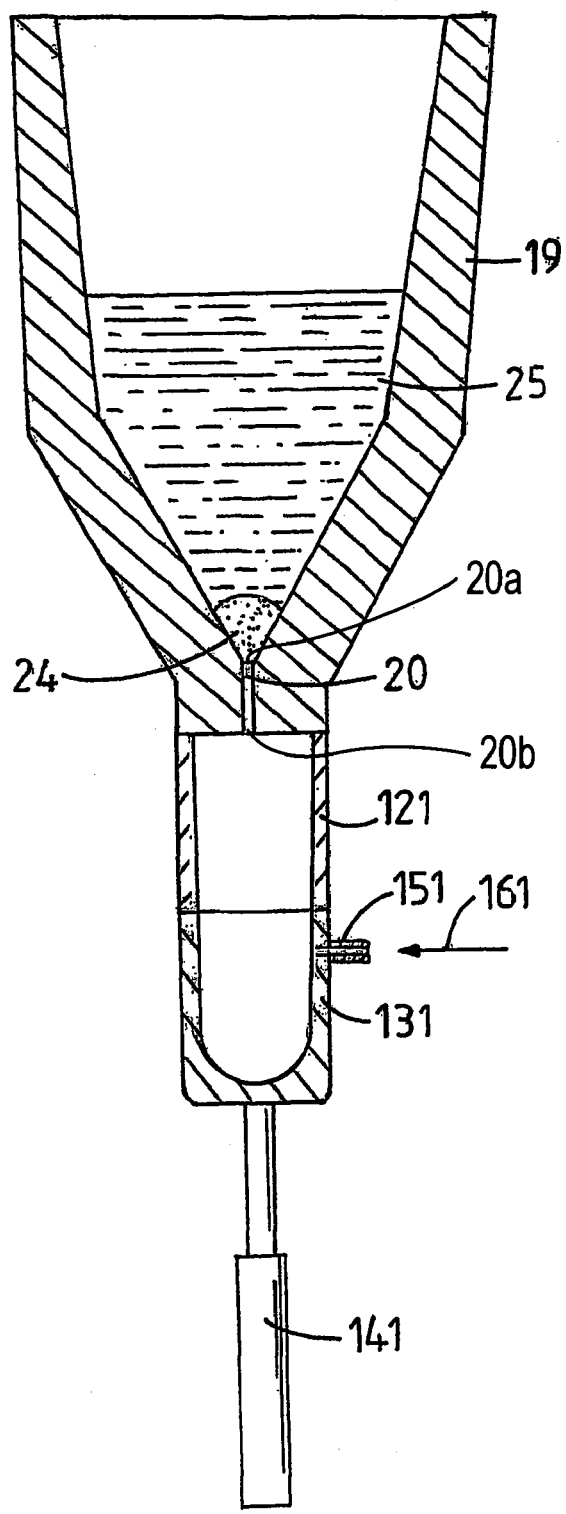
Figure 10:
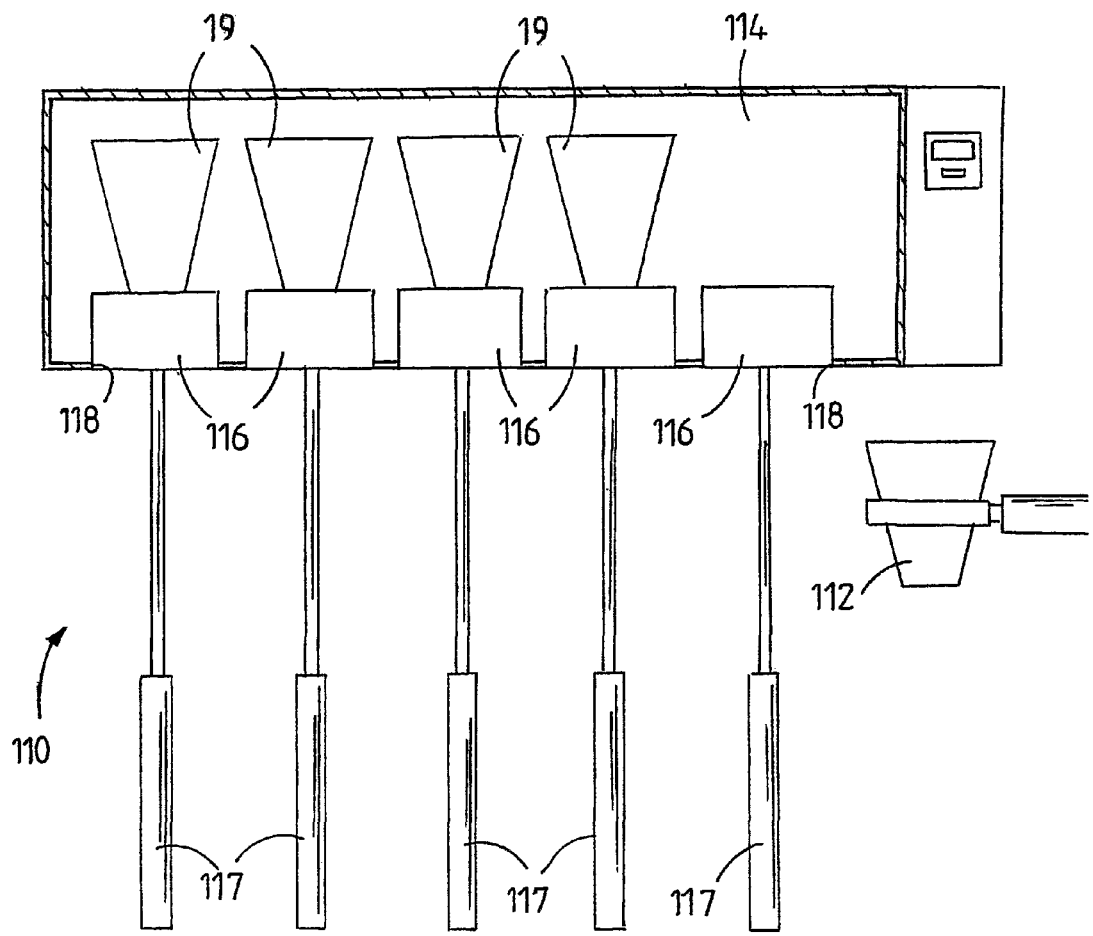
FIG. 10 and FIG. 11 are schematic elevations of a handling mechanism for introducing and removing reaction vessels into and from a heating furnace.
Figure 11:
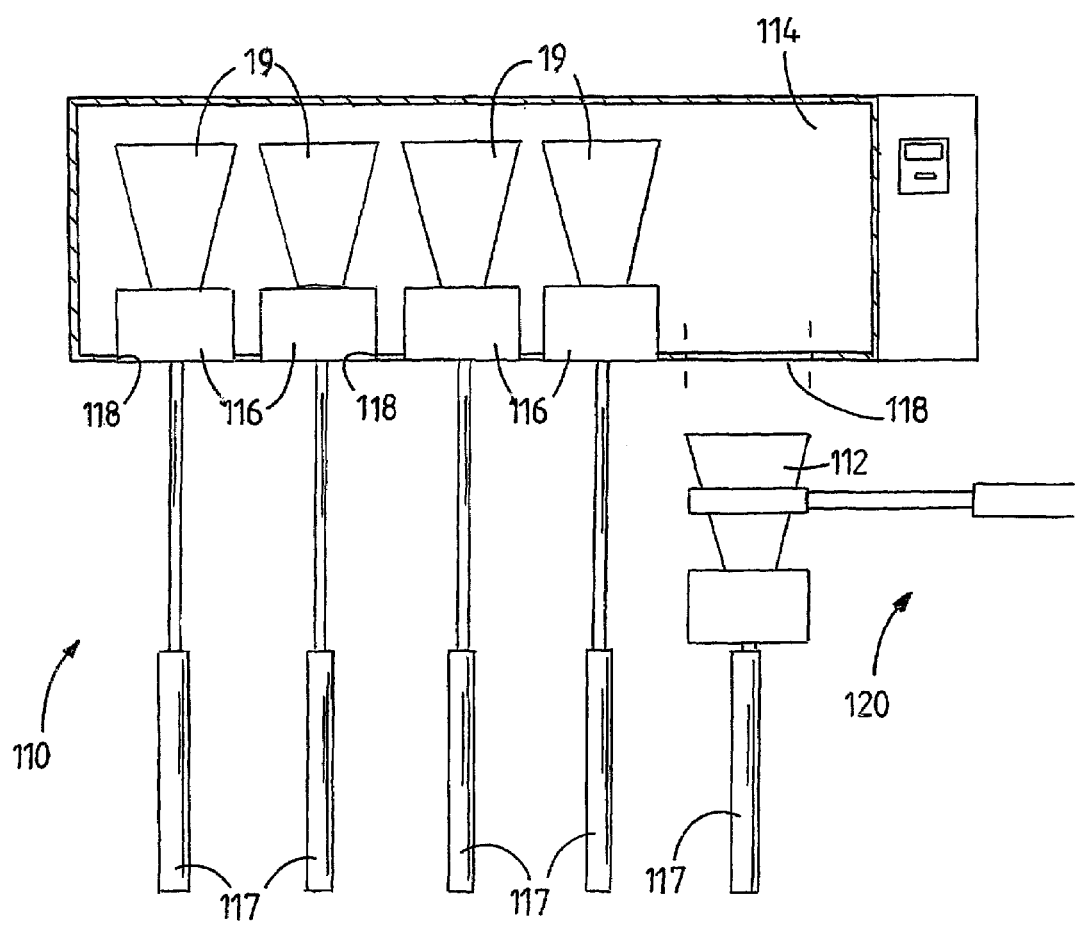

Alternatively with reference to FIGS. 9 and 10 oxygen can be introduced through the low level outlet 20 of the reaction vessel 19 via a collector vessel 131 and a tubular extension 121 of the reaction vessel 19.

The invention further provides for a methods of separating the molten collector/co-collector material 24 together with the gold or PGM's contained therein, from the molten slag 19.

EXAMPLE 1 OF A SEPARATING VESSEL

Figure 3:
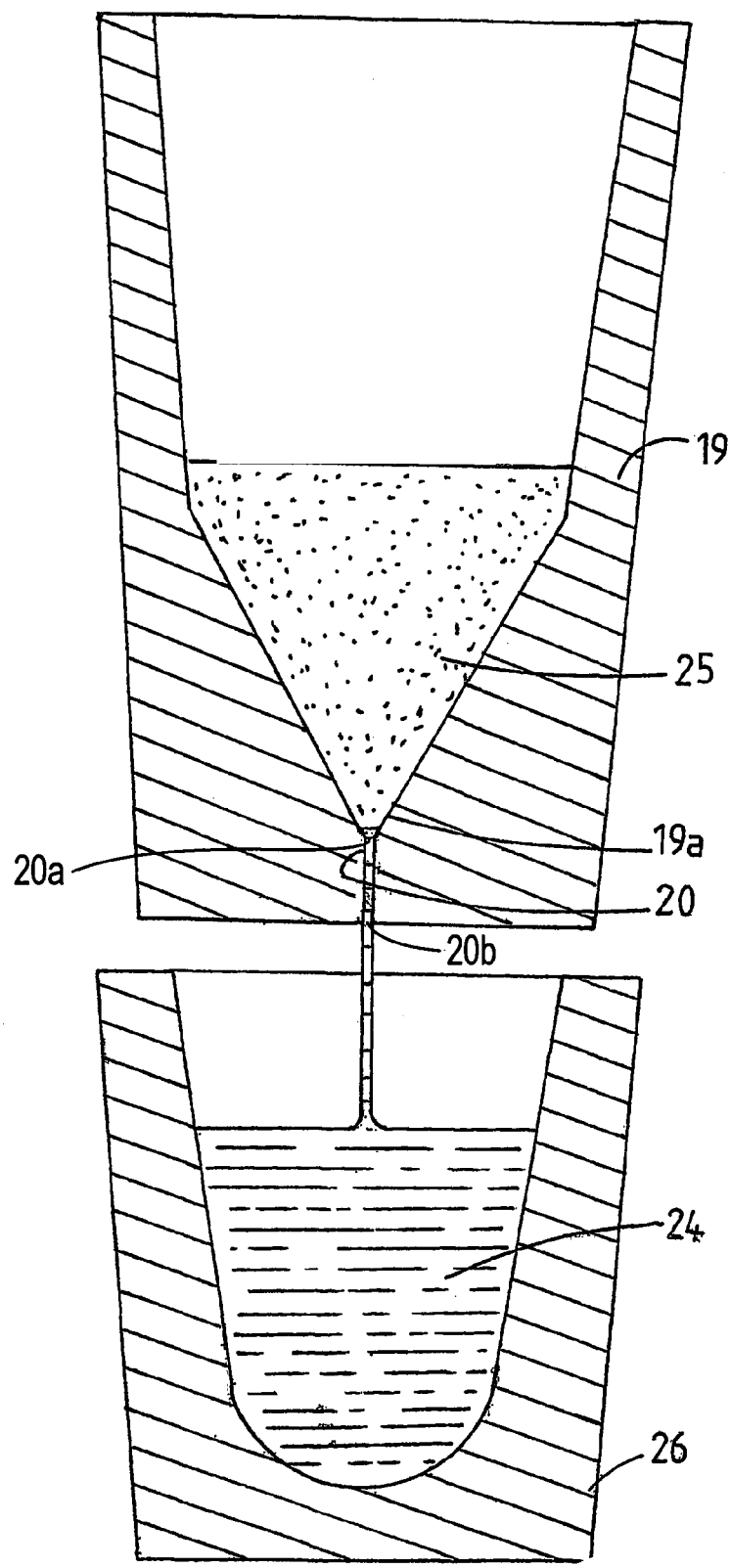

One method comprises the provision of a separating vessel 19 illustrated in FIGS. 2 and 3.

The vessel 19 is of a generally conical profile with the termination 19a of the cone facing downwardly. An outlet duct 20 is provided co-axially with the lower termination 19a of the cone 19, and is in the form of a linear passageway defined between its inlet and outlet apertures 20a, 20b, respectively. The outlet duct 20 is adapted in use to drain the collector material 24 from the vessel 19 into a suitable vessel or mould 26, FIG. 3. The invention envisages that the collector material 24 will be of a greater density and/or a lower viscosity than the molten slag 25 and the proportions of the outlet duct 20 will be such that only the collector material 24 is capable of flowing through the duct 20. Thus in the case of lead, the lead will readily drain through the outlet duct 20, while the molten slag 25 will be arrested at the outlet duct 20 and incapable of passing therethrough as a result of the lower density and/or greater viscosity thereof, as shown in FIG. 3. It has been found that an outlet duct 20 of generally circular cross-section with a diameter of between 0.5 mm and 2.0 mm preferably around 1.0 mm, will be suitable.

It will be appreciated that the size of the aperture could be rendered adjustable to suit requirements, for example by providing a suitable valve, not shown, or stopper for such outlet duct 20. One such arrangement is shown in FIG. 2 wherein the oxygen lance 23 terminates in a plug formation 22 which is axially movable between a position wherein it engages the lower end 19a of the vessel 19 to seal the outlet duct 20, and a position wherein the plug 22 is displaced from the lower end 19a of the vessel 19 to open the outlet duct 20. With such an arrangement therefor, the separating vessel 19 can also be utilized as a reaction vessel by closing the outlet duct 20 until separation of the collector material 24 and the slag 25 is required. Thus during fusion of the mixture 15, FIG. 1, and the step of oxidizing the collector material 16, FIG. 1, the plug 22 will be in its closed position. Subsequently, it will be opened to effect separation between the collector material 24 and the slag 25 as described above.

EXAMPLE 2 OF A SEPARATING A VESSEL

In this example with reference to FIGS. 4 to 7, a reaction and separating vessel 19 comprises a body member which defines an interior concavity 32 which includes a lowermost portion 32a for receiving a collector material 24 during an assaying procedure. Thus, during the process of causing fusion of a mixture of a flux material and a mineral sample, a collector material 24 in the form of lead or nickel sulfide or silver or the like is formed and serves to capture gold and PMG's present in the mineral sample. The collector material 24 being of greater density settles in the lowermost zone 32a of the reaction and separating vessel, while a slag 25 which includes gangue, overlies the collector material 24. As disclosed above, oxygen may be introduced into the collector material 24 to oxidize all, or a portion thereof, which is then reabsorbed in the slag 25.

The reaction and separating vessel 29 of the present disclosure is characterized in the provision of an outlet duct 20 which is located outside the lowermost zone 32a of the concavity 32, which receives the collector material 24. In the arrangements illustrated, the outlet duct 20 is located in the side wall of the vessel 29, but the invention is not limited to such a location and clearly other positions could also be functional.

It is a feature of the invention that the collector material 24, or the remainder thereof after oxidization, is separated from the slag 25 by rotating the reaction and separating vessel 29 transversely, so that the collector material 24 flows to the zone of the outlet duct 20, and is received in the outlet duct concavity 30. From the outlet duct concavity 30, the greater density and/or lower viscosity of the collector material 24 permits such material to be drained through the outlet duct 20, whereas the slag 25 is arrested and cannot flow through the duct 20. As disclosed above, the proportions of a circular outlet duct 20 could be between 0.5 mm to 2.0 mm, preferably 1.0 mm in diameter.

Preferably, the outlet duct 20 will include a concavity 30 into which the collector material 24 will flow prior to, or upon, being drained through the duct 20. If required, a groove or pathway, not shown, could also be provided on the inner surface of the vessel 29 to direct the collector material 24 from the lowermost portion 32a of the vessel 29 to the outlet concavity 30.

Figure 4:
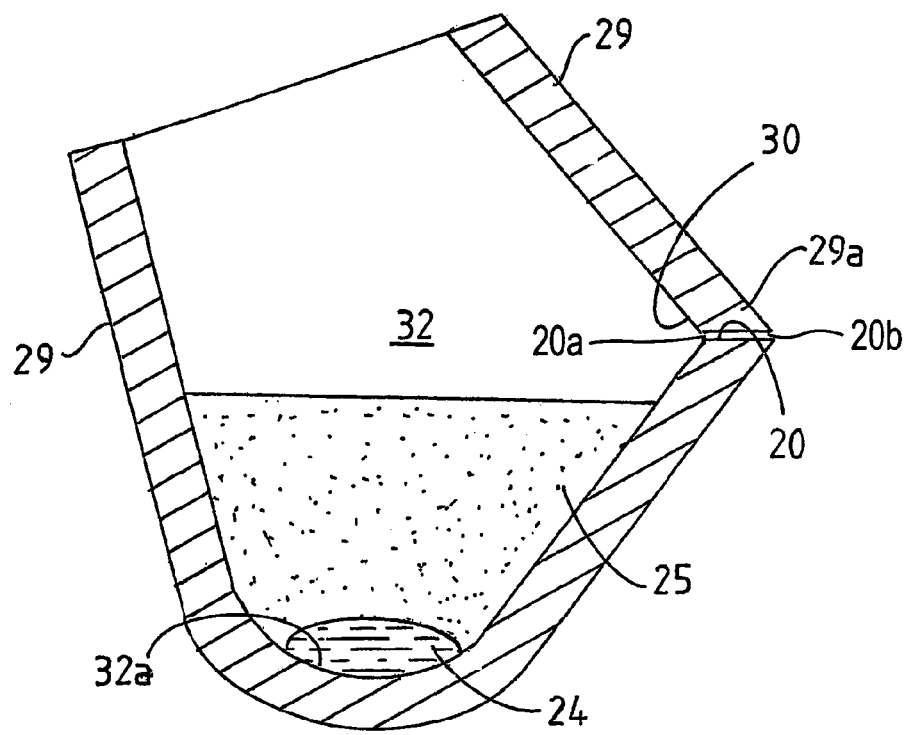
FIG. 4 and FIG. 5 are schematic sectioned elevations of a reaction and separating vessel which is employed in a method of assaying in accordance with the invention illustrating various steps in such method.
Figure 5:
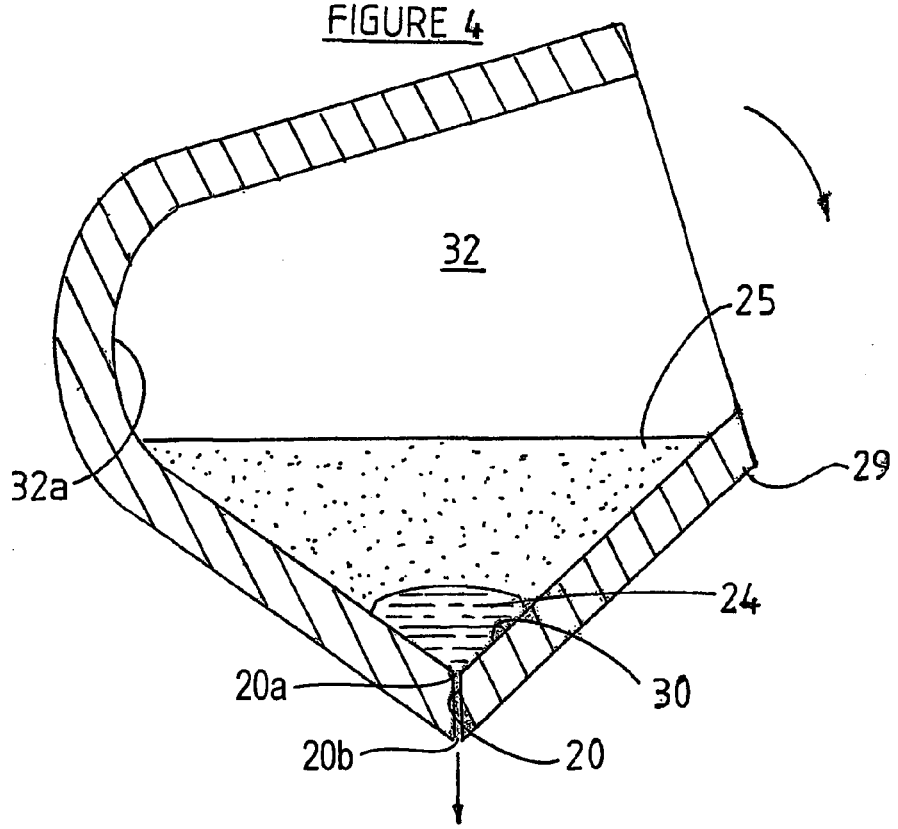

In the arrangement illustrated in FIGS. 4 and 5; the vessel 29 is rotated through approximately 90 degrees in order to position the outlet duct 20 at a lower-most position of the rotated vessel 29 for purposes of draining the collector material 24 therefrom. In the arrangement illustrated, the outlet duct 20 is disposed in a side wall of the vessel 29, but clearly this position can vary in accordance with the requirements, and could for example be disposed in a roof portion of the vessel. It will be understood that the position of the outlet duct 20 will determine the angle through which the vessel 29 should be rotated in order to cause the collector material 24 to flow to such outlet duct 20 for drainage purposes.

In the arrangement shown in FIGS. 4 and 5, the outlet duct concavity 30 is formed by an outward bulge 29a of the side wall of the vessel 29.

Figure 6:
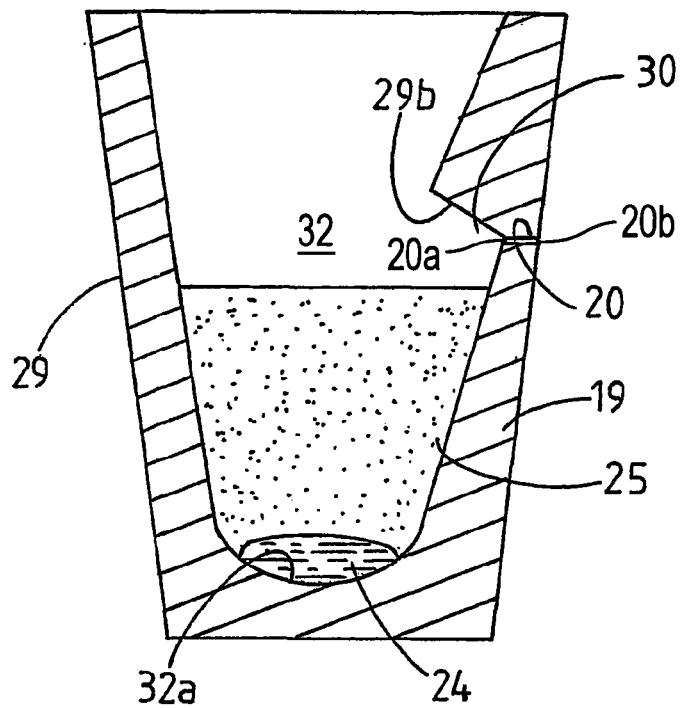
FIG. 6 and FIG. 7 are schematic sectioned elevations of a reaction and separating vessel which is employed in a method of assaying in accordance with the invention illustrating various steps in such method.
Figure 7:
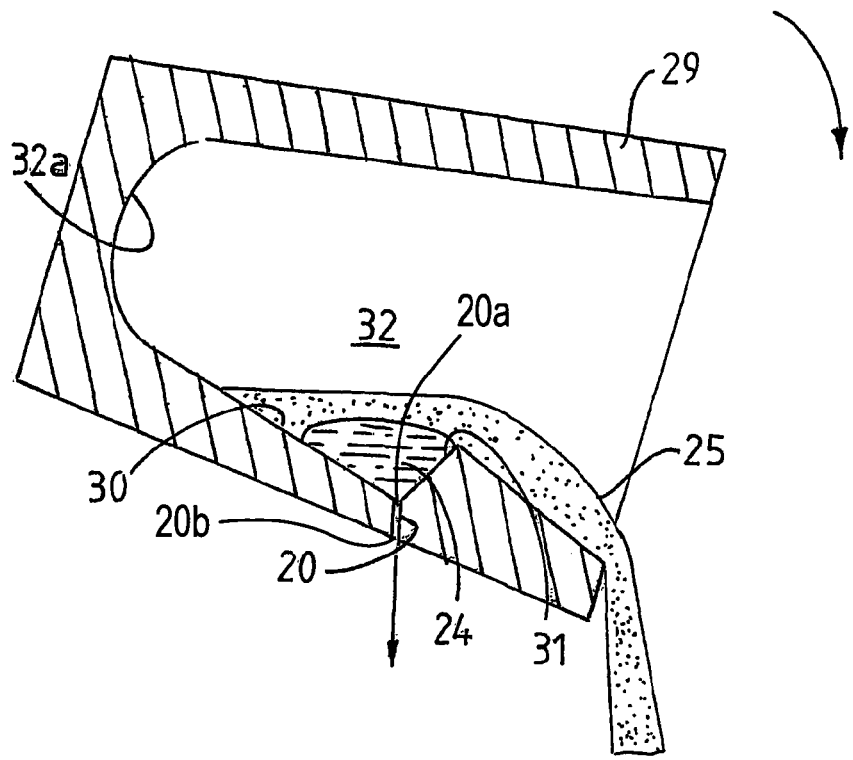

In an alternative arrangement shown in FIGS. 6 and 7, the outlet duct concavity 30 is formed by an inwardly directed shoulder 29b of the inner wall of the vessel 29. With this arrangement, the vessel will be rotated through an angle which is greater than 90 degrees in order to position the vessel 29 so that the outlet duct concavity 30 is disposed lower-most. In such a position, the slag 25, or at least a portion thereof, will overflow from the vessel 29 as shown in FIG. 7, and can be collected separately. Thus the arrangement will be such that all the slag 25 is decanted in such position, while the collector material 24 is drained through the duct 20.

In both examples described above, FIGS. 4 and 5 and FIGS. 6 and 7, the outlet duct 20 may be provided with valve or stopper means for selectively draining collector material 24 from the vessel.

EXAMPLE 3 OF A SEPARATING VESSEL

Figure 8:
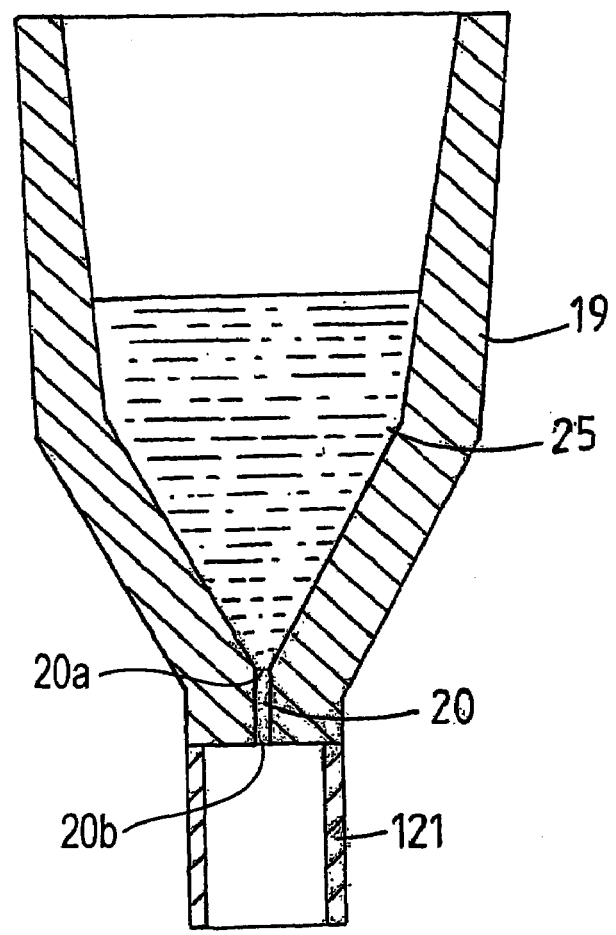
FIG. 8 and FIG. 9 are schematic sectioned elevations of a reaction and separating vessel which is employed in a method of assaying in accordance with the invention illustrating various steps in such method.
Figure 8:
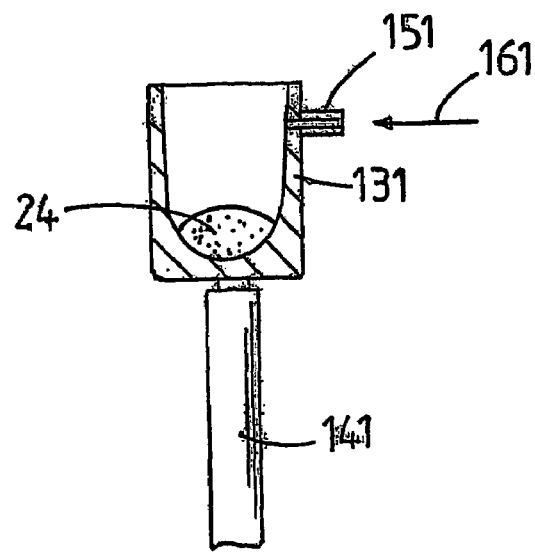

Referring to FIGS. 8 and 9 separating means for use in the assay method in accordance with the invention comprises a separation vessel 19 which is generally conically shaped and which terminates in a low level outlet duct 20. Below the outlet duct 20, a short length of ceramic tube 121 depends downwardly from their separation vessel 19.

The apparatus further includes a collection mould 131 which is disposed co-axially below the ceramic tube 121, and which is movably by means of a lifter 141 such as a hydraulic ram from a position removed from the ceramic tube as shown in FIG. 8; to a position wherein it sealingly engages the ceramic tube, FIG. 9. The collection mould 131 further includes a inlet 15 for oxygen 161 in the side wall thereof. With this arrangement, it is therefore possible to introduce oxygen 161 from a supply source, not shown into the separation vessel 10 via the interior of the collection mould 14 and through the outlet duct 11 from the separation vessel 10.

In an assaying method using the above apparatus, a mixture of a comminuted mineral sample, and a assaying flux will be introduced into a separation vessel. The flux will for example include lead oxide which will form slag and lead in a reaction process, the latter combining with the gold and/or PMG's as a result of chemical affinity. At this stage, heat is supplied to the separation vessel and/or material therein. The separation vessel may also be preheated as disclosed above. At this stage, the collection mould 131 will be engaged with the ceramic tube 121 oxygen 161ducted and introduced into the separation vessel 19 via the interior of the collection mould 13 land outlet duct 20 while the molten slag and lead is added to the separation vessel 19. Once sufficient time has elapsed, the oxygen supply is shut-off. At this stage the collector material such as lead has been re-oxidized to red oxide for absorption in the molten slag.

Pressure in the collection mould 131 will however at this stage limit discharge of material through the outlet duct 20 of the separation vessel 19. The next step of the process comprises lowering the collection mould 13 from the separation vessel 19 by means of the hydraulic ram 141, causing collected material 24 to drain through the outlet duct 20 into the collection mould 131. The diameter of the outlet duct 20 is such that the relatively dense and low viscosity collected material 24 will pass through the duct 20, while the slag 28 will be arrested within the vessel 19. The collection mould 131 which is relatively insulated from the heat of the separation vessel 19 by means of the ceramic tube 121 will be relatively cool and the collected material 24 will rapidly solidify in the collection mould 131, to form a prill of material. Thereafter the collection mould 131 can be tilted to discharge the prill 24 onto suitable conveying means, not shown, for further processing. At this stage also the separation vessel 19 can be tilted to discharge remaining slat 25 in the vessel 19 which is immediately available for re-use.

A further aspect of the invention comprises a handling mechanism whereby reaction vessels, crucibles, etc., which are used in a fire assay method can be loaded into and out of a furnace efficiently without undue loss of energy.

Such handling meachanism 10 consists of carrier means in the form of a number of level platforms 16 of refractory material, each of which are driven by a reciprocating ram 17, typically a pneumatic cylinder. Each platform 16 is movable between a first position in which it is displaced from the furnace 14 (shown in FIG. 2) and a second position in which it mates with a corresponding aperture 18 in the furnace 12 (shown in FIG. 1).

The apertures 18 are located in a base portion of the furnace 14 and each platform 16 is suitably dimensioned for mating with a complementary aperture 18 when the platform 16 is in the second position, effectively to close the aperture 18.

A loading device in the form of a robotic arm 20 is provided for loading/unloading the crucible 12 onto/from the platform 16 when the platform 16 is in the first position.

In use, a crucible 12 containing at least a mineral sample and flux is prepared for heat treatment in the furnace 14. One of the platforms 16 is moved into the first position, in which it is displaced from its complementary aperture 18 in the base portion of the furnace 14. The robotic arm 20 loads a crucible 12 onto the platform 16. The reciprocating ram 17 moves the platform 16 into the second position, and the crucible 12 is received into the furnace 14 through the aperture 18. The platform 16 mates with the aperture 18 so as effectively to close the aperture 18.

After the required residence time, the reciprocating ram 17 retracts, displacing the platform 16 away from the furnace 14, into the first position. When in the first position, the crucible 12 containing molten flux is removed from the platform 16 with the robotic arm 20. Once the crucible has been removed, the platform is moved back into the second position, to prevent heat escaping from the furnace 14 through the aperture 18.

It is envisaged that the handling mechanism will be useful in a fire assaying method in that sample carrying crucibles can be heated consecutively and on a continuous basis as opposed to a batch basis, to prevent heat escaping from the furnace when the crucibles are removed. Because the crucibles are not heated on a batch basis, the apparatus and method according to the invention has a further advantage in that the crucibles do not cool substantially, which reduces the time required to preheat the crucibles prior to assaying.

Yet a further aspect of the invention comprises the provision of a novel flux which has been found to provide a particularly rapid reaction time.

In one example of a flux in accordance with the invention, suitable for assaying of gold ores and Platinum Group element ores could typically have the following composition:

| | |
|---|---|
| Potassium hydroxide | 7.5% |
| Calcium hydroxide | 7.5% |
| Sodium hydroxide | 10% |
| Borax | 31% |
| Litharge | 30% |
| Sodium carbonate | 7.0% |
| Silica | 6.5% |
| Carbon | 0.5% | the above percentages being by weight.

In practice, the above composition will be used in quantities of approximately 200 grams for purposes of assaying gold ores and Platinum Group metal ores. For mine tailings quantities up to 500 grams might be used.

It has been found that the composition above, dramatically increases the rate of fusion of the flux during fire assay.

It has also been found that the action of the potassium hydroxide is further enhanced by the addition of sodium hydroxide. It has been found that a synergistic effect is created by the use of these two alkaline metal hydroxides.

The exact composition of the flux will vary in accordance with the types of ores to be assayed. Thus for example, the quantity of potassium hydroxide could vary between 5% and 60%, calcium hydroxide between 5% and 60%, and sodium hydroxide between 10% and 19%. In addition the flux composition could include fluorspar, red lead, potassium nitrate, and iron.

The advantages of the various aspects of the invention will be understood by persons skilled in the art. The processes of the invention readily lend themselves to mechanization and computerization. It will also be understood that the accuracy of the assaying process will be enhanced, and the time period required therefor, greatly reduced.

Doubtless variations of the invention in detail exist without departing from the principles set out in the consistory clauses. The invention is directed separately to a method of assaying as described above, as well as to a method of reducing the volume of a collector material, and/or concentrating in a co-collector material for the metal to be assayed, and also to a method and means for separating a collector/co-collector material from a molten slag.

The invention claimed is:

1. A method of assaying a mineral sample for determining the concentration of selected metals in a sample comprising the steps of:

providing a separating vessel having an outlet duct which includes an inlet aperture, an outlet aperture and a linear passageway defined between said inlet and outlet apertures;

providing a comminuted mineral sample;

mixing the mineral sample with a flux which forms a collector material during fusion thereof;

causing the mixture to fuse in the separating vessel whereby the mixture is transformed to a molten state to form a slag and to capture the metal to be assayed in the collector material; and separating the collector material from the slag by draining the collector material by force of gravity from the separating vessel through the linear passageway of the outlet duct while the slag remains within the separating vessel, the dimensions of the linear passageway proving the sole means which is sufficient to allow the collector material to drain therethrough by force of gravity but is sufficiently restricted to prevent the slag from draining therethrough by force of gravity, whereby the slag is retained within the separating vessel following separation of the collector material therefrom.

2. The method according to claim 1 wherein the reaction vessel is preheated prior to introducing the mixture into the reaction vessel to cause fusion of the mixture.

3. The method according to claim 1 wherein the method includes the step of oxidizing the collector material or portion thereof before or after fusion of the mixture to reduce the volume of the collector material.

4. The method according to claim 3 wherein the collector material is oxidized by introducing oxygen or an oxygen producing material into the reaction vessel after fusion of the mixture.

5. The method according to claim 3 wherein oxygen is introduced into the collector material by means of a lance.

6. The method according to claim 3 wherein oxygen is introduced into the collector material through a low level outlet aperture of the reaction vessel for oxidizing the collector material, prior to draining of the collector material through such outlet aperture.

7. The method according to claim 6 wherein oxygen is introduced into a separation vessel through the low level outlet aperture from a supply source via a collector mould which sealingly engages the separation vessel below the outlet aperture.

8. The method according to claim 7 including the step of disengaging the collection mould from the separation vessel after oxidization of the collector material to release pressure in the collection mould to permit the collector material to drain into such collection mould, through the outlet aperture.

9. The method according to claim 3 including the step of introducing an additional collector material which is resistant to oxidization into the reaction vessel, after or prior to fusion of the mixture and prior to oxidation of the collector material.

10. The method according to claim 9 wherein the additional collector material is silver or gold.

11. The method according to claim 1, including the step of separating the collector material from the slag after fusion of the mixture, and thereafter contacting the collector material with oxygen or oxygen forming material to oxidize the collector material or a portion thereof, to reduce the volume of the collector material.

12. The method according to claim 11 wherein a stream of oxygen gas is blown onto or into the collector material for oxidization purposes.

13. The method according to claim 1 wherein the outlet aperture for collector material is disposed at the lower extremity of the vessel.

14. A method according to claim 1 including the steps of separating the collector material from the slag comprising providing the separating vessel with an interior concavity which terminates in a lower portion for receiving the collector material, and which defines an outlet cavity in a position spaced from such lower portion, the outlet cavity including the linear passageway of the outlet duct for draining collector material from the outlet cavity by force of gravity, the dimensions of the linear passageway of the outlet duct being sufficiently restricted to prevent the slag from draining through the outlet duct by force of gravity, and comprising the further steps of rotating the separating vessel transversely so that the collector material in the lower-most portion flows to the outlet cavity; and draining such collector material from the outlet cavity through the outlet duct.

15. A method of assaying a mineral sample for the determination of the concentration of selected metals in the sample comprising the steps of:
providing a separating vessel having an outlet duct which includes an inlet aperture, an outlet aperture and a linear passageway defined between said inlet and outlet apertures;
preparing a mineral sample;
mixing the mineral sample with a flux which forms a collector material during fusion thereof; introducing the mixture into a reaction vessel;
causing the mixture to fuse in the separating vessel whereby the mixture is transformed to a liquid state to form a flux and to capture the metal to be assayed in the collector material;
separating the collector material from the slag by draining the collector material by force of gravity from the separating vessel through the linear passageway of the outlet duct while the slag remains within the separating vessel, the dimensions of the linear passageway providing the sole means which is sufficient to allow the collector material to drain therethrough by force of gravity but is sufficiently restricted to prevent the slag from draining therethrough by force of gravity, whereby the slag is retained within the separating vessel following separation of the collector material therefrom; and
before or after separating the collector material from the slag, contacting the collector material with oxygen or an oxygen forming material to oxidize the collector material or a portion thereof to reduce the volume of the collector material.

16. The method according to claim 15 wherein the collector material is oxidized by introducing oxygen or an oxygen producing material into the reaction vessel after fusion of the mixture, before separation of the collector material from the slag.

17. The method according to claim 16 comprising introducing oxygen into the collector material by means of a lance.

18. The method according to claim 16 wherein oxygen is introduced into the collector material through a low level aperture for draining collector material from the reaction vessel.

19. The method according to claim 15 wherein oxygen is introduced into the separation vessel through the low level aperture for draining collector material from the separation vessel from a supply source via a collector mould which sealingly engages the separation vessel below the outlet aperture.

20. The method according to claim 19 including the step of disengaging the collector mould from the separation vessel after oxidation of the collector material to permit collector material to drain into such collection mould, through the outlet aperture.

21. The method according to claim 15 including the step of introducing an additional collector material which is resistant to oxidization into the reaction vessel after or prior to fusion of the mixture and prior to oxidation of the collector material.

22. The method according to claim 21 wherein the additional collector material is silver or gold.

23. The method according to claim 15 including the step of separating the collector material from the slag formed during the fusion process, and thereafter contacting the collector material with oxygen or oxygen forming material to oxidize the collector material or a portion thereof to reduce the volume of the collector material.

24. The method according to claim 15 wherein a stream of oxygen gas is blown onto or into the collector material for oxidization purposes.

* * * * *